(12) United States Patent
Frechet et al.

(10) Patent No.: US 6,887,384 B1
(45) Date of Patent: May 3, 2005

(54) MONOLITHIC MICROFLUIDIC CONCENTRATORS AND MIXERS

(75) Inventors: Jean M. J. Frechet, Oakland, CA (US); Frantisek Svec, Alameda, CA (US); Cong Yu, Changchun (CN); Thomas Rohr, Vienna (AT)

(73) Assignee: The Regents of the University of California, Oakland, CA (US)

( * ) Notice: Subject to any disclaimer, the term of this patent is extended or adjusted under 35 U.S.C. 154(b) by 255 days.

(21) Appl. No.: 10/251,604

(22) Filed: Sep. 20, 2002

Related U.S. Application Data
(60) Provisional application No. 60/323,980, filed on Sep. 21, 2001.

(51) Int. Cl.[7] ............................................. B01D 15/08
(52) U.S. Cl. ..................... 210/634; 210/198.2; 210/502; 210/656; 264/45.1; 422/70; 422/101; 436/161; 366/340; 366/348
(58) Field of Search .......................... 210/198.2, 321.6, 210/501, 502.1, 500.42, 634, 635, 638, 650, 656, 321.84; 366/340, 348; 264/41, 45.1; 422/69, 70, 101; 436/161, 177, 178

(56) References Cited

U.S. PATENT DOCUMENTS

| | | | |
|---|---|---|---|
| 5,334,310 A | 8/1994 | Frechet et al. | 210/198.2 |
| 5,453,185 A | 9/1995 | Frechet et al. | 210/198.2 |
| 5,593,729 A | 1/1997 | Frechet et al. | 427/337 |
| 5,633,290 A | 5/1997 | Frechet et al. | 521/54 |
| 5,728,457 A | 3/1998 | Frechet et al. | 428/310.5 |
| 5,929,214 A | 7/1999 | Peters et al. | 530/417 |
| 6,238,565 B1 * | 5/2001 | Hatch | 210/635 |
| 6,596,988 B2 * | 7/2003 | Corso et al. | 250/288 |
| 6,616,825 B1 * | 9/2003 | Frechet et al. | 204/605 |
| 6,717,136 B2 * | 4/2004 | Andersson et al. | 250/288 |
| 2002/0043499 A1 * | 4/2002 | Hammen et al. | |

OTHER PUBLICATIONS

Cong Yu, et al., Monolithic Porous Polymer for On–Chip Solid–Phase Extraction and Preconcentration Prepared by Photoinitiated in situ Polymerization Within a Microfluidic Device, *Anal. Chem.*, 73:5088–5096, (2001).

Thomas Rohr, et al., Porous Polymer Monoliths: Simple and Efficient Mixers Prepared by Direct Polymerization in the Channels of Microfluidic Microfluidic Chips, *Electrophoresis*, 22:3959–3967, (2001).

Gerard J. M. Bruin, Recent Developments in Electrokinetically Driven Analysis on Microfabricated Devices, *Electrophoresis*, 21:3931–3951 (2000).

O. T. Guenat, et al., Partial Electroosmotic Pumping in Complex Capillary Systems; Part 2: Fabrication and Application of a Micro Total Analysis System ($\mu$TAS) Suited for Continuous Volumetric Nanotitrations, *Sensors and Actuators*, B 72:273–282 (2001).

Dirk Bökenkamp, et al., Microfabricated Silicon Mixers for Submillisecond Quench–Flow Analysis, *Anal. Chem.*, 70:232–236 (1998).

Richard D. Oteschuk, et al., Trapping of Bead–Based Reagents Within Microfluidic Systems: On–Chip Solid–Phase Extraction and Electrochromatography, *Anal. Chem.*, 72:585–590 (2000).

(Continued)

Primary Examiner—Joseph Drodge
(74) Attorney, Agent, or Firm—Peters, Verny, Jones & Schmitt, LLP

(57) ABSTRACT

Microfluidic devices comprising porous monolithic polymer for concentration, extraction or mixing of fluids. A method for in situ preparation of monolithic polymers by in situ initiated polymerization of polymer precursors within microchannels of a microfluidic device and their use for solid phase extraction (SPE), preconcentration, concentration and mixing.

42 Claims, 5 Drawing Sheets

OTHER PUBLICATIONS

Michael Lämmerhofer, et al., Chiral Monolithic Columns for Enantioselective Capillary Electrochromatography Prepared by Copolymerization of a Monomer with Quinidine Functionality. 1. Optimization of Polymerization Conditions, Porous Properties, and Chemistry of the Stationary Phase, *Anal. Chem.*, 72:4614–4622 (2000).

Jennifer A. Tripp, et al., Grafted Macroporous Polymer Monolithic Disks: A New Format of Scavengers for Solution–Phase Combinatorial Chemistry, *J. Comb. Chem.*, 3:216–223 (2001).

Shaofeng Xie, et al., Porous Polymer Monoliths: Preparation of Sorbent Materials with High–Surface Areas and Controlled Surface Chemistry for High–Throughput, Online, Solid–Phase Extraction of Polar Organic Compounds, *Chem. Mater*, 10:4072–4078 (1998).

Núria Masqué, et al., Synthesis and Evaluation of a Molecularly Imprinted Polymer for Selective On–Line Solid–Phase Extraction of 4–Nitrophenol from Environmental Water, *Anal. Chem.*, 72:4122–4125 (2000).

Julia Khandurina, et al., Microfabricated Porous Membrane Structure for Sample Concentration and Electrophoretic Analysis, *Anal Chem.*, 71:1815–1819 (1999).

Philip Dell'Oreo, et al., Monitoring Process–Scale Reactions Using API Mass Spectrometry, *Anal. Chem*, 71:5165–5170 (1999).

Stephen C. Jacobson, et al., Microfluidic Devices for Electrokinetically Driven Parallel and Serial Mixing, *Anal. Chem.*, 71:4455–4459 (1999).

Joselito P. Quirino, et al., On–Line Concentration of Neutral Analytes for Micellar Electrokinetic Chromatography. 5. Field–Enhanced Sample Injection with Reverse Migrating Micelles, *Anal. Chem.*, 70:1893–1901 (1998).

Bing He, et al., A Picoliter–Volume Mixer for Microfluidic Analytical Systems, *Anal. Chem.*, 73:1942–1947 (2001).

Cong Yu, et al., Towards Stationary Phases for Chromatography on a Microchip: Molded Porous Polymer Monoliths Prepared in Capillaries by Photoinitiated in situ Polymerization as Separation Media For Electrochromatography, *Electrophoresis*, 21:120–127 (2000).

Fiona G. Bessoth, et al., Microstructure for Efficient Continuous Flow Mixing, *Anal. Commun.*, 36:213–215 (1999).

Gregor Ocvirk, et al., Optimization of Confocal Epifluorescence Microscopy for Microchip–based Miniaturized Total Analysis Systems, *Analyst*, 123:1429–1434 (Jul. 1998).

Debashis Dutta, et al., Dispersion Reduction in Pressure–Driven Flow Through Microetched Channels, *Anal. Chem.*, 73:504–513 (2001).

Jing Ni, et al., Electrochemically Actuated Mercury Pump for Fluid Flow and Delivery, *Anal. Chem.*, 73:103–110 (2001).

Tinglu Yang, et al., Fabrication of Phospholipid Bilayer–Coated Microchannels for On–Chip Immunoassays, *Anal. Chem.*, 73:165–169 (2001).

Cong Yu, et al., Monolithic Porous Polymer for On–Chip Solid–Phase Extraction and Preconcentration Prepared by Photoinitiated in Situ Polymerization Within A Microfluidic Device, *Anal. Chem.*, 73:5088–5096 (2001).

Thomas Rob et al., Porous Polymer Monoliths: Simple and Efficient Mixers Prepared by Direct Polymerization in the Channels of Microfluidic Chips, *Electrophoresis*, 22:3959–3967 (2001).

Christopher T. Culbertson, et al., Electroosmotically Induced Hydraulic Pumping on Microchips: Differential Ion Transport, *Anal. Chem.*, 72:2285–2291 (2000).

*Upchurch Scientific*, Spec. Sheets, https://www.upchurch.com/Products/specsheet.asp?vSpecSheet=74. printdate: Jan. 8, 2003.

Robin H. Liu, et al., Passive Mixing in a Three–Dimensional Serpentine Microchannel, *Journal of Microelectromechanical Systems*, 9/2:190–197 (Jun. 2000).

Gregor Ocvirk, et al., High Performance Liquid Chromatography Partially Integrated Onto a Silicon Chip, Research Articles.

* cited by examiner

MONOLITHIC MICROFLUIDIC CONCENTRATORS AND MIXERS

This application is based on and claims priority of the Provisional application Ser. No. 60/323,980, filed on Sep. 21, 2001.

This invention was made in the course of contract DE-AC03-76SF00098 between the United States Department of Energy and the University of California for the operation of Lawrence Berkeley Laboratory. The United States Government has certain rights to this invention.

BACKGROUND OF THE INVENTION

1. Field of the Invention

This invention concerns microfluidic devices comprising porous monolithic polymer suitable for extraction, preconcentration, concentration and mixing of fluids. In particular, the invention concerns microfluidic devices comprising monolithic polymers prepared by in situ initiated polymerization of monomers within microchannels of a microfluidic device and their use for solid phase extraction, preconcentration and mixing.

2. Background and the Related Disclosures

The interest in microfabricated devices designed for micro-total analytical systems ($\mu$-TAS) is growing rapidly.

A number of applications for analytical microchips in areas such as enzymatic analysis, polymerase chain reaction (PCR), immunoassay, DNA sequencing, hybridization, mapping, isoelectric focusing, capillary zone electrophoresis, as well as capillary electrochromatography have already been reported. The first products involving microfluidic chip designed for the gel electrophoretic analysis of biopolymers are now commercially available, for example, from Agilent Technologies. These products were shown to compete successfully with classical techniques, such as polyacrylamide gel electrophoresis (PAGE).

Microanalytical systems with more complex architectures have also been reported, for example, in *Electrophoresis,* 21:3931–3951 (2000); *Anal. Chem.,* 70:232–236 (1998); *Sens. Actuat. B-Chem.,* 72:273–282 (2001); *Anal. Chem.,* 69:3646–3649 (1997); and *Science,* 273:205–211 (1996).

Despite the usefulness of microfluidic chips in a variety of applications, some problems with their use still persist. For example, almost all reported microfluidic chips feature open channel architecture where the surface to volume ratio is rather small. This presents a serious problem in applications such as chromatographic separations, heterogeneous catalysis, and solid phase extraction that rely on interactions with a solid surface. Since the only solid surface within these chips is the channel wall, the chip can handle only minute amounts of compounds.

The issue of surface area in the macroscopic devices can be solved by packing them with porous particles that significantly increase the available surface area and also enable the introduction of specific chemistries into the device. Early attempts to pack a microchip channel with beads were less successful (*Anal. Meth. Instrum.,* 2:74 (1995)). *J. Anal. Chem.,* 72:585 (2000), for example, describes a device for solid phase extraction by packing octadecyl silica beads from a side channel into a specifically designed cavity of the microchip.

A few reports have dealt with attempts to enhance the limited surface area in channels of a microchip without packing. For example, *J. Chromatogr.,* 853:257 (1999), reports fabricated microchip channels containing arrays of ordered tetragonal posts. Electrokinetic preconcentration of DNA from dilute samples using porous silicate membrane incorporated into the microchip has also been reported. Selecting the pore size which permits passage of electric current but prevents passage of large molecules has enables their concentration (*Anal. Chem.,* 71:1815 (1999)).

Another technique enabling an increase in the concentration of desired compounds involves sample stacking, a technique successfully used in capillary electrophoresis. (*Anal. Chem.,* 70:1893 (1998). However, this approach is only practical for electrodriven systems. In contrast, solid-phase extraction (SPE) is a more general method since it enabled handling of large sample volumes regardless of the method used to ensure sample flow (*Anal. Chem.,* 72:4122 (2000)).

In the early 1990s, macroscopic rigid porous monoliths prepared in situ by a thermally initiated polymerization process were introduced and are disclosed, for example, in U.S. Pat. Nos. 5,334,310; 5,453,185 and 5,593,729. Their use has been described in a number of applications including HPLC and CEC of small molecules, chiral compounds, proteins, peptides, and nucleic acids (*Anal. Chem.,* 72:4614 (2000)). The monolithic technology has also been successfully applied to the preparation of devices for scavenging undesired compounds from solutions and for SPE (*J. Comb. Chem.,* 3:216 (2001)); *Chem. Mater.,* 10:4072 (1998)) and good control over both porous properties and surface chemistry of the monolithic polymers was achieved.

Yet another of the persisting problems of microfluidic chip technologies is also the lack of efficient mixing within the channels. The simplest solution to the mixing problem is the use of so called T-piece. For example, parallel mixing has been demonstrated at various mixing ratios using a series of T-intersections (*Anal. Chem.,* 71:5165 (1999)). However, this does not solve the problem of the lack of turbulences and using this approach, mixing within a substantial channel length can only be achieved at low flow velocities. An increase in mixing efficiency has been observed after dividing both phases into a larger number of small parallel channels, mixing the streams in each of these channels, and recombining the sub-streams again into a single channel. In this approach, enhancement of the mixing results from the increase in contact area between the two phases (*Anal. Commun.,* 36:213 (1999)).

A somewhat similar strategy involves splitting the streams in an array of small laminae followed by their recombination in a triangular chamber (*Sens. Actuat. B-Chem,* 72:273 (2001)). A picoliter-volume mixer with a wave-like architecture that includes multiple intersecting channels of varying lengths having a bimodal width distribution was recently introduced (*Anal, Chem.,* 73:1942 (2001)). This approach enhanced both lateral and longitudinal mixing and the device performed efficiently.

Still another implementation includes a three-dimensional serpentine microchannel design with a "C-shaped" repeating unit fabricated in a silicon wafer (*J. Microelectromechanical Systems,* 9:190 (2000)).

The manufacture of all of the micromixers discussed above involves the use of typical microfabrication techniques. Both, rather complex designs and very small features, can easily be fabricated in substrates such as glass or silicon. However, production of devices with very fine features using polymer-based substrates and the use of fabrication techniques such as hot embossing and injection molding is still lagging.

Previously, these inventors demonstrated that the porous properties of the monolithic polymers can be controlled within a broad range by pore size. However, the thermally initiated free radical polymerization used originally was not well suited for the preparation of monolithic structures within microdevices since selective heating of specific areas of the microchip to locate the monolith strictly within the assigned space was difficult to achieve. This problem was subsequently overcome by the development of UV initiated polymerization processes, described in *Electrophoresis*, 21:120 (2000), which is similar to the photolithographic patterning used in microelectronics. Photopolymerization enables the formation of monoliths only within a specified space. The polymerization reaction is strictly confined within the areas exposed through a mask, while no polymerization occurs in unexposed zones.

It is therefore a primary objective of the current invention to provide a microfluidic device comprising a microchannel filled with a polymerization mixture that is solidified by an in situ initiated polymerization into a monolithic polymer with a specific properties permitting a solid phase extraction, concentration, preconcentration and mixing of fluids.

All patents, patent applications and publications cited herein are hereby incorporated by reference.

SUMMARY

One aspect of the current invention is a microfluidic device for extracting, concentrating or mixing of fluids, said device comprising a porous polymer monolith placed within a microchannel enabling fluid flow, wherein said microchannel is filled with a polymerization mixture that is solidified by an in situ initiated polymerization into a monolithic polymer permitting solid phase extraction, concentration, preconcentration and mixing.

Yet another aspect of the current invention is a microfluidic device for extracting, concentrating or mixing, wherein said device comprises a porous polymer monolith within a microchannel enabling fluid flow, wherein said polymer monolith comprises polymerized monomer units bearing a hydrophilic group, a precursor of a hydrophilic group, an ionizable group, a hydrophobic group, an affinity ligand, or a mixture thereof, wherein said microchannel enabling fluid flow is contoured into a glass, fused silica, quartz, or plastic inert substrate.

Still another aspect of the current invention is a polymer monolith consisting of an array of interconnected microglobules and pores having a pore size permitting a passage of fluids at a variety of flow velocities.

Yet another aspect of the current invention is a method for fabrication of microfluidic device comprising a channel filled with a polymerization mixture that is solidified by an in situ photoinitiated polymerization of a polymer precursor into a monolithic polymer permitting solid phase extraction, concentration, preconcentration and mixing.

Still yet another aspect of the current invention is a method for fabricating a microfluidic device suitable for extraction, concentration, or mixing, said method comprising steps:

(a) providing an inert solid substrate;
(b) generating a single or multiple microchannels contoured into said solid substrate;
(c) forming a polymerization mixture by admixing a monovinyl monomer, a cross-linking polyvinyl monomer, an initiator, and a porogenic solvent;
(d) introducing the polymerization mixture into a microchannel within a microfluidic device; and
(e) initiating the in situ polymerization of the mixture, thereby forming a monolithic polymer within the microfluidic channel, wherein said monomer comprises a hydrophilic group or a precursor of a hydrophilic group selected from the group consisting of 2-hydroxyethyl methacrylate, 2-hydroxyethyl acrylate, glycidyl methacrylate, glycidyl acrylate, acetoxystyrene, t-butoxycarbonyloxystyrene and a combination thereof, or an ionizable group selected from the group consisting of an amino group, a carboxylic acid group, a sulfonic or phosphoric acid group represented by acrylic acid, methacrylic acid, itaconic acid, maleic anhydride, styrene sulfonic acid, 2-acrylamido-2-methyl-3-propanesulfonic acid, 2-(methacryloxy)ethyl phosphate, acrylic amide of amino acid, methacrylic amide of amino acid, 2-vinylpyridine, 4-vinylpyridine, 2-(dialkylamino) ethyl acrylate, methacrylate 2-(dialkylamino)ethyl, 2-(morpholino)ethyl acrylate, 2-(morpholino)ethyl methacrylate, [2-(methacryloxy)ethyl]trimethylammonium chloride, [2-(methacryloxy)ethyl]trimethylammonium methylsulfate, and a combination thereof, or a hydrophobic group selected from the group consisting of acrylate esters, methacrylate esters, acrylate amides, methacrylate amides, styrene, styrene derivatives, and a combination thereof, and optionally, an affinity ligand selected from the group consisting of polysaccharides, antibodies, enzymes, lectins, antigens, cell surface receptors, intracellular receptors, viral coat proteins, DNA, and a mixture thereof.

Another aspect of the current invention is a method for solid phase extraction, preconcentration and mixing of a fluid.

BRIEF DESCRIPTION OF DRAWINGS

FIG. 5 shows elution pattern of green fluorescent protein from hydrophobic monolithic concentrator. Conditions: loading: 200 $\mu$L of 18.5 nmol/L protein solution in 8 mmol/L TRIS-HCl buffer (pH 8) containing 0.95 mol/L ammonium sulfate, flow rate 3 $\mu$L/min. Elution: 1:1 acetonitrile-water at a flow rate of 3 $\mu$L/in.

Definitions

Figure 1A:
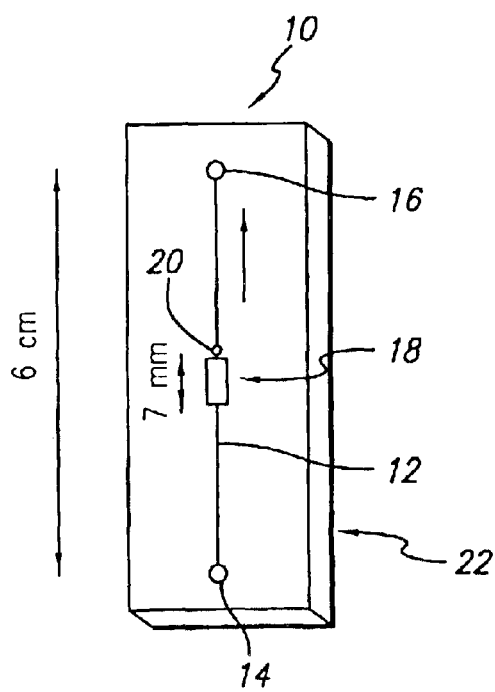
FIG. 1A is a schematic representation of a microfluidic device showing a monolithic concentrator positioned within a microchannel.

As used herein, the term:

"Monolith", "monolithic polymer", "polymer monolith" or "polymeric monolith" means a continuous porous polymer structure that is disposed in the microfluidic device across its entire internal cross-section area. The monolith is prepared from a mixture of monomers polymerized in situ to produce a single piece of a chemically cross-linked porous polymer.

DETAILED DESCRIPTION OF THE INVENTION

The present invention generally relates to microfluidic devices, polymeric monoliths, a method of fabrication of said devices and monoliths, a method for mixing, concentrating or extraction of compounds. The devices and polymeric monoliths of the invention are suitable for preparing and handling fluidic samples. Specifically, these devices are useful for solid phase extraction, concentration, preconcentration and mixing.

Briefly, a present device comprises one or several microfluidic channels contoured into an inert substrate and a monolithic porous polymer produced by polymerization in situ within said microfluidic channel. By changing chemical properties, pore size, and porosity of the polymer the control is achieved over the flow resistance and sorption properties of the monolith. Different physical and chemical properties of monoliths in desired areas enable the formation of co-contiguous zones of porous materials performing or responsible for different functions.

I. Microfluidic Devices

Microfluidic devices of the invention are structures comprising one or a multiplicity of microchannels contoured into a surface of a solid inert substrate wherein said microchannel, completely or partially filled with a monolithic porous polymer, enables a fluid flow through said polymer.

The microfluidic devices are suitable for extracting, concentrating or mixing of fluids.

A general design of the microfluidic device of the invention is illustrated in FIG. 1. FIG. 1A shows a device 10 containing a solid inert support 22 and a microchannel 12 containing a monolith 18. The monolith 18 may function as a concentrator or extractor. The device further contains an inlet 14 and outlet 16 openings for introduction and removal of the fluid from the device. The fluid flows between these two openings. The direction of flow is indicated by an arrow.

A compound to be concentrated, eluted or extracted is introduced into the device through the inlet 14 in the fluid which is then run through the polymeric monolith 18. The extraction or elution of compounds is monitored by any suitable means for detection of said compounds at the detection point 20. The means for detection can be any suitable technique known in the art for these purposes, such as for example, a laser, induced fluorescence, chemiluminescence, radioactivity, UV spectroscopy, and any other such detection method.

Figure 1B:
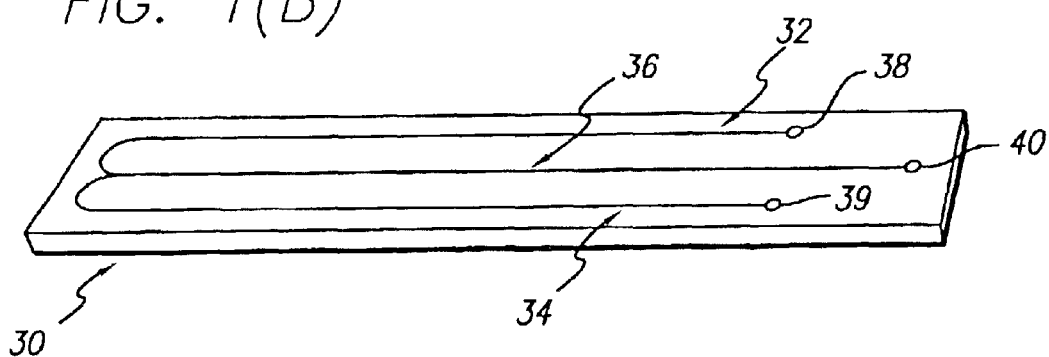
FIG. 1B is a schematic representation of a microfluidic device showing two microchannels and a mixing area of the monolithic mixer positioned withing said device with FIG. 1C showing magnification of the mixing area and FIG. 1D showing placement of the photo mask over the microchannels to achieve selective in situ polymerization only in the mixing area.
Figure 1C:
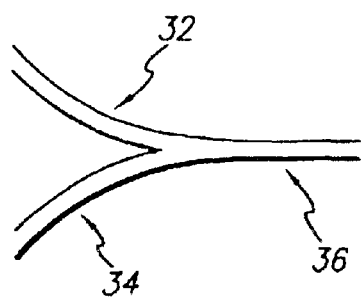
Figure 1D:
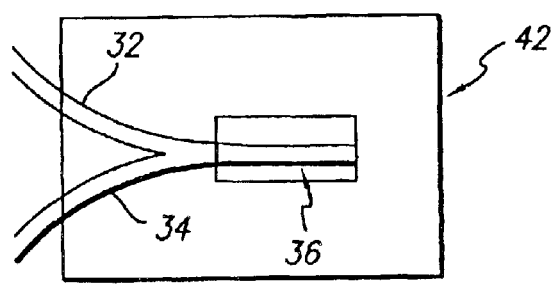

In alternative, the monolith is used as a mixer. The microfluidic device comprising a monolithic mixer is illustrated in FIGS. 1B–1D wherein FIG. 1B is a schematic representation of the mixer layout within the device 30 showing two microchannels 32 and 34, mixing area 36, two inlets 38 and 39 and outlet 40. FIG. 1C is a magnified view of two microchannels 32 and 34 and the mixing area 36 and FIG. 1D shows a position of the photo mask 42 used for the selective in situ polymerization of the monolithic mixer.

The fluids to be mixed are introduced into the microchannels 32 and 34 which may or may not be filed with the monoliths through inlets 38 and 39, run through these microchannels into the mixing area 36, where they are mixed and the mixed solution is collected at the outlet opening 40. The mixing area contains a monolith having appropriate mixing properties.

The size, length, width, depth and shape of the device and/or microchannel are variable and depend on the intended use and function of the device.

II. Design and Function of Microfluidic Devices

Microfluidic devices of the invention are designed according to their intended function.

The microfluidic device according to the invention comprise at least an inert substrate, with a single or multiple microfluidic channels and a porous polymeric monolith.

A. Inert Substrate

A supporting structure of the device is typically a block made of an inert solid substrate. Such inert solid substrate may be any material which does not react with compounds used for preparation of the polymeric monoliths and compounds used in the concentrating, extracting or mixing steps. Examples of these materials are fused silica, glass, quartz or plastic.

B. Microchannels

The microchannels are miniaturized grooves or channels contoured into the inert material of a substrate. Microchannels are generated mechanically or chemically by engraving, milling, cutting, etching, embossing or contouring into a surface of the inert substrate.

Sizes and dimensions of microchannels are variable and may have any length, width and depth which is suitable for their intended use.

The microchannel can be straight, serpentine, circular or have any other geometry and is typically from about 1 to about 200, preferably about 100 $\mu$m wide, and from about 10 to about 70, preferably 60 $\mu$m deep, depending on the intended use of the device.

The microchannel is fully or partially filled with a porous polymeric monolith.

C. Polymeric Monolith

A polymeric monolith deposited within the microchannel is a porous material which permits fluid to flow through its pores.

1. Polymerization Mixtures

The polymeric monolith is made of monomers present in a mixture which is suitable for in situ polymerization resulting in formation of such porous monolithic polymer. Such mixture comprises, for example, a monomer or a mixture of monomers, solvent or a mixture of solvents and an initiator.

Typically, the polymeric monolith comprises polymerized monomer units bearing a hydrophilic group, a precursor of a hydrophilic group, an ionizable group or a precursor thereof, a hydrophobic group or a precursor thereof, or their mixtures. Optionally, the polymeric monolith may also contain an affinity ligand. Any combination of the above monomer units is intended to be within the scope of the invention.

In the porous polymer monoliths which comprise polymerized monomers bearing a hydrophilic group or a precursor to a hydrophilic group, such monomer is generally an acrylate, methacrylate or styrene selected from the group consisting of 2-hydroxyethyl methacrylate, butyl methacrylate, 2-hydroxyethyl acrylate, glycidyl methacrylate, glycidyl acrylate, acetoxystyrene, chloromethylstyrene, t-butoxycarbonyloxystyrene, and a combination thereof.

In the porous polymer monoliths which comprise polymerized monomer units bearing a hydrophobic group or a precursor to a hydrophobic group such monomer is generally selected from the group consisting of acrylate esters, methacrylate esters, acrylate amides, methacrylate amides, styrene, styrene derivatives, and a combination thereof wherein the preferred monomers comprising the hydrophobic group are alkyl acrylates, alkyl methacrylates, styrenes, alkylstyrenes or a combination thereof.

In the porous polymer monoliths which comprise polymerized monomer units bearing an ionizable group or a precursor to the ionizable group such polymerized monomer generally contains a functionality such as an amino group, a carboxylic acid group, a sulfonic and phosphoric acid group with a preferred ionizable monomer selected from the group consisting of acrylic acid, methacrylic acid, itaconic acid, maleic anhydride, styrene sulfonic acid, 2-acrylamido-2-methyl-3-propanesulfonic acid, 2-(methacryloxy)ethylphosphate, acrylic amide of amino acid, methacrylic amide of amino acid, 2-vinylpyridine, 4-vinylpyridine, 2-(dialkylamino) ethyl acrylate, methacrylate 2-(dialkylamino)ethyl, 2-(morpholino)ethyl acrylate, 2-(morpholino)ethyl methacrylate, [2-(methacryloxy)ethyl] trimethylammonium chloride, [2-(methacryloxy)ethyl] trimethylammonium methylsulfate, and a combination thereof.

Preferred monomers for fabrication of the monoliths are acrylates, methacrylates and derivatives thereof.

The porous polymeric monolith additionally comprises a cross-linking monomer.

The cross-linking monomer is a preferably a polyvinyl monomer selected from the group consisting of a diacrylate, dimethacrylate, triacrylate, trimethacrylate, diacrylamide, dimethacrylamide, or a divinylaromatic monomer with preferred polyvinyl monomers being ethylene diacrylate, ethylene dimethacrylate, trimethylolpropane triacrylate, trimethylolpropane trimethacrylate, methylenebisacrylamide, or piperidinediacrylamide, divinylbenzene or divinylnaphthalene.

In one preferred embodiment, the porous polymer monolith comprises from about 10 to about 90% of one or more monovinyl monomers, from about 5 to about 90% of one or more polyvinyl monomers and from about 0.01 to about 2% of the initiator, with respect to the monomers.

The porous polymer monoliths of the invention may optionally also comprise from about 1 to about 50%, of an affinity ligand. The ligand is either covalently immobilized within the already formed monolith or is added to a polymeric mixture before polymerization in a form of a monomer. The ligand may be a biological or a synthetic compound, wherein the biological affinity ligand is selected from the group consisting of polysaccharides, antibodies, enzymes, lectins, antigens, cell surface receptors, intracellular receptors, viral coat proteins, DNA, and a mixture thereof, and wherein the synthetic affinity ligand is selected from the group consisting of reactive dyes, tannic acid, gallic acid, iminodiacetic acid, ethylenediaminetriacetic acid, inert salt of [2-(methacryloyloxy)ethyl]dimethyl(3-sulfopropyl)ammonium hydroxide, and a mixture thereof.

2. In situ Polymerization

The monoliths of the invention are fabricated by in situ initiated polymerization.

In situ polymerization may be any process or procedure which will effectively polymerize the polymerization mixture into the monolithic structure when such mixture is deposited within the microchannel. The in situ polymerization process will produce a porous solid monolith. Such process may be initiated by heating, redox reaction or photoinitiation.

The polymerization may be triggered by locally heating selected areas of the monolith to effect polymerization or by UV light in a process similar to the standard photolithography used for patterning in microelectronics, or by redox reactions.

Preferred initiation is achieved via UV irradiation. The photoinitiation permits the use of masks to obtain channels or regions within the channels filled with a solid polymer. The use of specifically designed masks also allows the formation of co-contiguous zones of porous materials with desired physical and chemical properties in different areas of the chip.

Polymerization is generally initiated by an initiator such as UV photoinitiator, thermal initiator or redox initiator added to a monomer mixture. The polymerization is initiated under conditions such as the irradiation with ultraviolet light, admixing of the redox components, such as ammonium peroxodisulfate and N,N,N',N'-tetramethylene-1,2-ethylenedimanine, or with the heating to a temperature from about 30° C. to about 120° C.

The initiator of the in situ polymerization is either a photoinitiator, redox, or thermal initiator. The photoinitiator is generally selected from the group consisting of benzophenone, dimethoxyacetophenone, xanthone, and thioxanthone and the photoinitiated polymerization is performed by UV irradiation of the polymerization mixture comprising the photoinitiator. The thermal initiator is generally a peroxide, a hydroperoxide, or an azocompound selected from the group consisting of benzoylperoxide, potassium peroxodisulfate, ammonium peroxodisulfate, t-butyl hydroperoxide, azobisisobutyronitrile, and azobisisocyanobutyric acid and the thermally induced polymerization is performed by heating the polymerization mixture to temperatures between 30° C. and 120° C. The redox initiator is selected from the group consisting of mixtures of benzoyl peroxide-dimethylaniline, and ammonium peroxodisulfate-N,N,N',N'-tetramethylene-1,2-ethylenediamine.

In situ photopolymerization was used for preparation of polymeric monoliths described above. UV initiators were added and the polymerization mixtures were exposed to UV light source, such as, for example, an Oriol deep UV illumination system (Stratford, Conn.) fitted with a 500 W HgXe-lamp.

Radiation power of the UV lamp was measured with different probe heads at wavelengths 254, 260, 280, 310, 365, 400 and 436 nm. At these wavelengths, the UV-lamp generated radiation power 8.16; 11.15; 2.31, 6.32; 2.83; 3.92; and 2.25 mW/cm$^2$, respectively. In the alternative, the polymerization mixtures may be exposed to two or more UV light sources generating cumulatively the intensity within the range listed above.

The in situ photopolymerization carried out as described herein results in a channel containing a macroporous polymer monolith.

3. Porous Properties of Monoliths

An important feature of the polymeric monolith intended for the flow-through applications is its permeability to fluids. Such permeability depends on its porous properties.

The porous properties, which effectively control the flow resistance, of the monolithic device are pore size, distribution and porosity. These properties are affected by the composition of the polymerization mixture.

Both the flow resistance of monoliths in HPLC mode and the flow velocity in monolithic CEC columns have been previously demonstrated to be inversely proportional to the pore size. Therefore, in order to obtain monolithic devices with the desired flow properties it is important to control the porous properties.

The porosity of the monolith can be controlled by changing the composition and percentage of porogenic solvents in the polymerization mixture.

Since the pore size of the polymer monolith plays such an important role, porosity measurement were performed.

Table 1 lists porous properties obtained from mercury intrusion porosimetry for monoliths prepared from two different polymerization mixtures.

TABLE 1

| Monolith | 1 | 2 |
|---|---|---|
| Total intrusion volume (mL/g) | 1.28 | 1.30 |
| Median pore diameter ($\mu$m) | 1.0 | 10.7 |
| Porosity (%) | 50 | 50 |
| Back pressure (MPa) | 0.9 | 0.01 |

Monolith 1 was prepared from the polymerization mixture containing 2-hydroxyethyl methacrylate as a monomer, ethylene dimethacrylate as a cross-linking agent, 1-dodecanol and cyclohexanol as porogenic solvents and 2,2-dimethoxy-2-phenylacetophenone (DAP) as initiator. Polymerization time was six minutes.

Monolith 2 was prepared from the polymerization mixture containing 2-hydroxyethyl methacrylate as a monomer, ethylene dimethacrylate as a cross-linking agent, methanol and hexane as porogenic solvents and 2,2'-azobisisobutyronitrile (AIBN) as the initiator.

Back pressure at a flow rate of 1 $\mu$L/min was recalculated to a monolith length of 1 cm.

Results seen in Table 1 show that although the median pore sizes for monoliths 1 and 2, namely 1.0 $\mu$m for monolith 1 and 10.7 $\mu$m for monolith 2, differ dramatically, both monoliths have very similar pore volume of 1.3 mL/g representing a porosity of 50%. The size of pores is directly proportional to the flow resistance. The large pores within the polymer material minimize the flow resistance, enabling achievement of high flow rates of up to 10 $\mu$L/min without causing mechanical breakage of the monolith.

The low flow resistance of monolith according to this invention enables high flow rates of up to 10 $\mu$L/min, which corresponds to a linear flow velocity of 50 mm/s and far exceeds the flow velocities typical of the other available analytical microchips.

The monoliths are formed of solid, rounded, sphere-like polymeric microglobules clustered together. Each microglobule structure has a diameter of from about 5 to about 20 $\mu$m. Accumulation of these clusters generate the porous polymer monolith which contains multiple pores of the same or variable sizes and shapes. These pores have typically sizes from about 30 nm to about 20 $\mu$m, preferably from about 1 $\mu$m to about 10 $\mu$m.

According to the present invention, the pore sizes range depends on the selected polymerization mixture and particularly on use of the porogenic solvent.

In order to achieve the desired pore structure, polymerization must be performed in the presence of porogenic solvents. The porogenic solvent are essential part of the polymerization mixtures. Their function is first to dissolve all monomers and the initiator, second to form a homogeneous solution and third to control the phase separation process during polymerization.

Typically, the porogenic solvent is water, an organic solvent or a mixture thereof. The porogenic organic solvent is selected from the group consisting of hydrocarbons, alcohols, ketones, aldehydes, organic acid esters, ethers, soluble polymer solutions, and mixtures thereof such as cyclohexanol, 1-dodecanol, methanol, hexane, propanol, dodecanol, ethylene glycol, butanediol, methyl-t-butylether, diisopropylketone, butanol ethyl acetate, butyl acetate, poly (methyl methacrylate), and mixtures thereof.

The solvent is typically present in an amount from about 30 vol % to about 80 vol %, with preferred range from about 40 vol % to about 60 vol %.

The preferred porogenic mixture consists of methanol and hexane.

To test suitability of the porogenic solvents, two monoliths were prepared using polymerization mixtures containing a large percentage of these porogenic solvents. These monoliths were prepared from monomers suitable for preparation of ion exchange (IE) and hydrophobic (HI) concentrators. Compositions of polymerization mixtures and specific surface areas are shown in Table 2.

TABLE 2

| Surface Areas of IE and HI Concentrator Monoliths | | |
|---|---|---|
| Monolith | IE | HI |
| EDMA (g) | 0.48 | 0.48 |
| HEMA (g) | 0.5857 | — |
| META (g) | 0.1541 | — |
| BMA (g) | — | 0.7191 |
| AIBN (mg) | 12 | 12 |
| Methanol (g) | 2.52 | 2.52 |
| Hexane (g) | 1.08 | 1.08 |
| Pores size ($\mu$m) | 13.2 | 19.5 |
| Pore volume (mL/g) | 3.48 | 3.85 |
| Surface area ($m^2$/g) | 1.3 | 0.7 |

Reaction conditions:

The polymeric mixtures indicated in the Table 2 were UV irradiated at room temperature for 3 hours;
  Ethylene dimethacrylate (EDMA);
  2-Hydroxyethyl methacrylate (HEMA);
  [2-(methacryloyloxy)ethyl]trimethyl ammonium chloride (META);
  Butyl methacrylate (BMA);
  Azobisisobutyronitrile (AIBN).

Both IE and HI monoliths listed in Table 2 were characterized by very large pores of 13.2 $\mu$m (IE) and 19.5 $\mu$m (HI) and a pore volume of 3.48 and 3.85 mL/g, respectively, that provide the monoliths with a low flow resistance and allow the use of high flow rates.

As seen in Table 2, the ion-exchange (IE) concentrator was prepared from a polymerization mixture comprising EDMA, META and HEMA dissolved in methanol/hexane porogenic solvent by polymerization initiated with AIBN. Since the quaternary ammonium functionality of META is a strong base, the monolith prepared from this mixture exhibits properties typical of strong anion exchangers. The addition of HEMA increases the hydrophilicity of the polymer thus reducing the undesired hydrophobic interactions with the probe or sample and allows control of the loading of the monolith with the ionizable repeat units.

The hydrophobic monolith (HI) also seen in Table 2 was obtained from a polymerization mixture of BMA and EDMA dissolved again in methanol/hexane solvent and AIBN acting as a polymerization initiator. This monomer has definite hydrophobic properties.

4. Flow-Through Properties of Monoliths

The polymeric monoliths are specifically designed for use in the flow-through mode. Concentration, extraction or mixing are processes occurring inside of the monolith. The efficacy of these processes, however, depends on the flow rate and flow resistance. Therefore, a flow resistance as low as possible is an important objective.

All porous monoliths prepared and used herein have preferably a porosity of 50% or more.

Pumps, such as mechanical pumps described, for example in *Anal. Chem.*, 73: 504–513 (2001); *Anal. Chem.*, 73: 103–110 (2001); *Anal. Chem.*, 72: 2285–2291 (2000) and *Analyst*, 123: 1435–1441 (1998) or electroosmotic flow (EOF) as described, for example in *Anal. Chem.*, 73: 165–169 (2001) may be conveniently used in these monoliths to achieve desired flow rate through the monoliths of the invention. In this regards, the use of EOF is convenient since it does not afford any pressure within the channel.

However, electrically driven flow can only be used with a limited number of solvents and requires the use of electrolytes with low ionic strength to avoid excessive generation of the heat.

III. Fabrication of Microfluidic Device

The devices according to the invention are fabricated as a solid unit made of an inert substrate material. The substrate material includes one or several microchannels, depending on the intended function. These channels are contoured mechanically or chemically by engraving, milling cutting, etching, embossing or using any other suitable technique which enables formation of the microchannel of the predetermined length, width and depth within a surface of the inert substrate.

A method for fabrication of the polymer monolith of the invention comprises steps of:

(a) providing an inert solid substrate;

(b) generating a single or multiple microchannels contoured into said solid substrate;

(c) forming a polymerization mixture by admixing an appropriate monomer, a cross-linking monomer, an initiator, and a porogenic solvent;

(d) introducing the polymerization mixture into a microchannel within a microfluidic device; and (e) initiating the in situ polymerization of the mixture, thereby forming a monolithic polymer within the microfluidic channel.

IV. Monolithic Concentrators and Mixers

1. Monolithic Concentrators

Using the above described method for fabrication of the microfluidic device, the monoliths particularly suitable for concentration (monolithic concentrators) and solid phase extraction (SPE monoliths) were prepared. The devices prepared according to the current invention are better suited for their concentration or extraction function than the previously available devices.

Monolithic concentrators are microdevices that concentrate highly diluted compounds.

Sample preconcentration is a critical operation generally required for the determination of trace amounts of compounds of interest for which the concentration in the original solution exceeds the detection limits of the detection method. This is even more important in the case of microfluidic device related applications given the very small volumes of samples that can be handled within the microdevice.

In SPE, samples are adsorbed on porous materials with appropriate chemistry to effect pre-concentration and later released using a stronger eluent. In addition to the significant increase in concentration of the sample, the use of selective SPE devices may also eliminate interfering compounds.

One utility for the microchips of the current invention are microfluidic devices for SPE. The microscale preparation of porous polymer monoliths that combines well-controlled porous properties with appropriate surface chemistry using in situ, preferably UV, initiated polymerization is well-suited for the in situ fabrication of solid phase extraction (SPE) microdevices.

A method for preparation of these devices is simple and straightforward. Such method leads to porous monoliths with a number of different surface chemistries. To demonstrate the monolithic technology in the context of solid phase extraction (SPE), two different types of monoliths, namely ion-exchange and hydrophobic monoliths, were investigated. The functionality of these devices was demonstrated on adsorption and release of small molecules, peptides, and proteins.

Ion-Exchange Concentrator

The concentrator with ion-exchange functionalities adsorbs compounds with the opposite charge. A monolithic concentrator comprising a monomer mixture containing META was fabricated by the in situ polymerization. The concentrator was first conditioned using a 1:1 mixture of 0.1 mol/L HCl and acetonitrile followed by loading a specific volume of a probe solution. Coumarin 519 (C-519), which is a carboxylic acid, was selected as the probe molecule. Desorption was achieved using a 10 s pulse of a selected salt solution. A number of salts including sodium chloride, fluoride, sulfate, and carbonate were tested. Preferred are sulfate and carbonate ions. Particularly preferred is sodium salicylate.

Hydrophobic Concentrators

Hydrophobic concentrators are monoliths prepared from the mixtures comprising a hydrophobic monomer or a mixture of hydrophobic monomers, as described above.

Many analytical systems, such as, for example, a microfluidic system used in protein mapping might make use of a protein digestion followed by separation of the resulting peptide fragments and their identification by mass spectroscopy. Such systems may require preconcentration of a protein from its dilute solution prior to its enzymatic digestion and a second concentration prior to their injection in the separation part of the device. Therefore, the enrichment or concentration of peptide and protein probes using the hydrophobic concentrator was investigated.

The monolith's performance was demonstrated with the enrichment of a hydrophobic tetrapeptide.

For these studies, a conjugate of coumarin 519 and the tetrapeptide phe-gly-phe-gly was adsorbed onto the butyl methacrylate based monolithic concentrator. Since the conjugate is per se very hydrophobic, complete adsorption was achieved from its aqueous solution. Results are described in Example 7.

Similar studies were carried out with green fluorescent protein (GFP) for which an increase in concentration by a factor as high as $10^3$ was achieved.

Various types of concentrators which are currently available were compared. Table 3 shows a comparison of the capacity of the current concentrator with two concentrators prepared by other methods.

TABLE 3

Capacity of Concentrators Prepared by Different Methods

| Method | Probe | Flow rate (nL/s) | Elution volume (nL) | Capacity (mol) |
|---|---|---|---|---|
| Functionalized channel | C-460 | 0.16 | 0.48 | $2.2 \times 10^{-16}$ |
| Channel cavity packed with beads | BODIPY | 1.2 | 0.33 | $2.8 \times 10^{-15}$ |
| Channel with monolith | C-519 | 50 | 35 | $1.9 \times 10^{-10}$ |

C-519 is Coumarin 519.
C-460 is Coumarin 460.
BODIPY is 4,4-difluoro-4-bora-3a,4a-diaza-s-indacene.

As seen in a comparative Table 3 of two concentrators prepared by different methods with the concentrator of the invention, the adsorption capacity for the current device is $1.9 \times 10^{-10}$, that is 5–6 orders of magnitude larger than that of open (functionalized) channel of which capacity is $2.2 \times 10^{-16}$ and channel cavity filled with ODS beads where the capacity is $2.8 \times 10^{-15}$ mols.

The current concentrators thus have substantially larger capacity.

2. Monolithic Mixers

In the second aspect, this invention provides monolithic mixers which are able to mix two or more fluids.

Such mixing is required for success in a number of operations such as sample injection, gradient elution, in situ derivatization, and chemical reactions. Therefore, mixers, mixing devices of the invention, have been developed. These devices may be conveniently incorporated into the microfluidic devices of the invention as separate entities in combination, for example, with concentrators or separators.

Monolithic mixers are typically prepared from mixtures consisting of one or several monomer-crosslinker combinations, such as, for example, a combination of HEMA-EDMA. The chemistry and properties of the mixers may easily be changed by choosing different monomer combinations. This ability to prepare micromixers with surface properties tuned for mixing in specific environments is an important asset in building dedicated microfluidic systems.

The process used for the preparation of monolithic materials enables a broad range of variations of their porous properties and internal morphology and is easily amenable to the microfluidic device format. The porous monoliths appear to be well suited for the preparation of mixing microdevices.

Mixing behavior of various polymers was also studied.

TABLE 4

| Monolith | A | B | C | D |
|---|---|---|---|---|
| 2-Hydroxyethyl methacrylate | 24 | 9 | 6 | 3 |
| Ethylene dimethacrylate | 16 | 6 | 4 | 2 |
| 1-Dodecanol | 42 | 41.1 | 43.5 | 45.9 |
| Cyclohexanol | 18 | 43.9 | 46.5 | 49.1 |
| DAP | 1 | 1 | 1 | 1 |
| Reaction time, min | 6 | 20 | 30 | 40 |

The performance of the monolithic mixers A–D prepared according to Table 4 has been tested by pumping aqueous solutions of two fluorescent dyes at various flow rates and monitoring the point at which the boundary of both streams completely disappeared. Properties, such as porosity, median pore diameter and back pressure of the monolith A have been shown in Table 1 as monolith (1).

Figure 7:
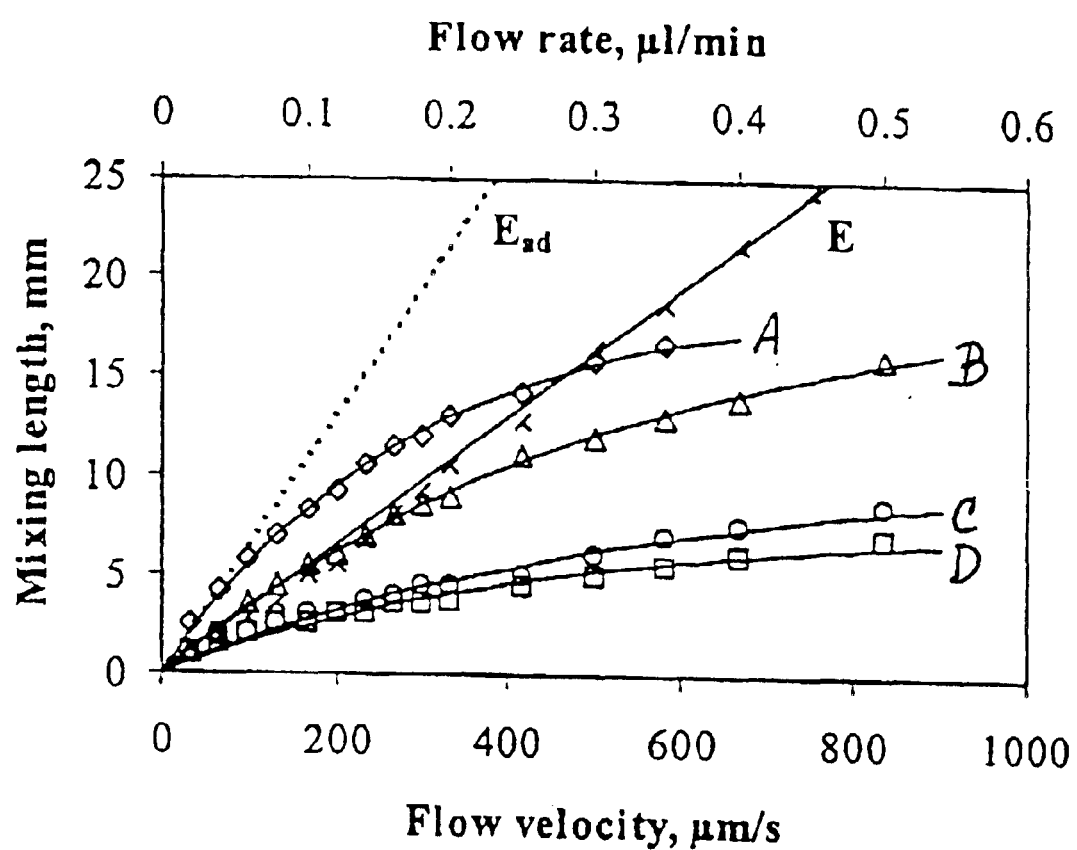
FIG. 7 shows a length of the flow path required to achieve complete mixing in an empty channel (-X-), and channel containing porous polymer monoliths A (-◇-), B (-△-), C (-○-), and D (-□-). The dashed line ($E_{ad}$) represents the length calculated for an empty channel with a cross section adjusted to 50%.

Results of mixing experiments are seen in FIG. 7. FIG. 7 shows a length of the flow path required to achieve complete mixing in an empty channel (E), and channel containing porous polymer monoliths (A), (B), (C), and (D). The dashed line ($E_{ad}$) represents the length calculated for an empty channel with a cross section adjusted to 50%.

Results seen in FIG. 7 show the mixing performance of more porous monoliths prepared from polymerization mixtures that include 60% to 95% of porogen. While the mixing length of monolith (B) prepared from a mixture containing 15% monomers is similar to that of monolith (A), monolith (C) and (D) afford much better mixing. The plots clearly demonstrate the increased efficiency of mixing over that of all other monoliths. Best results were achieved with a monolithic mixer containing very large irregular pores.

V. Complex Microfluidic Devices

Use of the in situ polymerization of specifically selected polymerization mixtures using UV photoinitiation is a new approach developed and described in this invention.

The microfluidic devices of the invention are suitable for concentration, extraction or mixing purposes.

UV initiated polymerization within the channels of a microfluidic device is a simple and versatile approach that enables a single step preparation of polymeric monoliths with a wide variety of chemistries and porous properties at the desired location. This approach enables the design and preparation of numerous building blocks instrumental for the development of complex microfluidic systems. These could be conveniently utilized as building entities in more complex devices permitting analysis and detection of environmental or biological samples.

Complex microfluidic devices may contain a variety of additional functional elements with specific functions. For example, the device may additionally contain other components then concentrator, solid phase extractor or mixer, such as, for example an enzymatic reactor, or separation column. Some of these may be made of different polymers mixtures polymerized in situ within the microchannel, said mixtures having differently defined chemical and/or physical properties resulting in different functionality.

These additional elements could be positioned in front of the microchannel, between two or more elements or sequentially connected to the effluent side of the microchannel. For example, an SPE element can be introduced between the reactor and the separation column, thereby permitting accumulation of the products flowing from the reactor into the SPE unit from which they may be eluted at the desired time by applying a small volume of an eluent only to the SPE. Introduction of the polymeric concentrator of the invention before the detection device may, for example, permit detection of much smaller amounts of an analyte, contaminant or another chemical entity of which detection was not possible because the minuscule amounts present in the sample. In the alternative, the device could have two or more microchannels.

Monoliths or microdevices of the invention, as described above, can be conveniently used in systems enabling detection of biological materials such as peptides, proteins, DNA, RNA in synthetic or biological fluids or suspensions of cells or tissues.

Example 1

Fabrication of Microfluidic Device for Solid Phase Extraction in Ion-Exchange Mode A simple straight microchannel 100 μm wide, 40 μm deep, and 6 cm long etched in a borosilicate glass and covered with another bonded glass plate was washed with acetone, water, and filled with 0.2 mol/L NaOH for 30 min, washed with water, filled with 0.2 mol/L HCl for 30 minutes, washed again with water and acetone, and dried in an oven at a temperature of 120° C. for 1 hour. The microchannel was then vinylized by filling the microchannel with a 30% solution of 3-(trimethoxysilyl)propyl methacrylate in acetone and allowed to react at room temperature in the darkness for 24 hours. The vinylized microchannel was then washed with acetone and dried using a stream of nitrogen.

Polymerization mixture was prepared by dissolving 0.48 g ethylene dimethacrylate, 0.59 g 2-hydroxyethyl methacrylate, 0.15 g [2-(methacryloyloxy)ethyl]trimethyl ammonium chloride, and 12 mg azobisisobutyronitrile in a mixture of 2.52 g methanol and 1.08 g hexane. All these compounds are commercially available from Aldrich, Milwaukee, Wis.

This mixture was purged with nitrogen for 10 min to remove any oxygen present. The microchannel was completely filled with the deaerated polymerization mixture using a pipette and the openings sealed with tape. The surface of the chip was then covered with a mask that had an open window allowing a specific section of the microchannel to be exposed to the UV light.

The microchannel was then covered with foil except for the 7 mm long window, and exposed to UV light in a photoreactor equipped with two 365 nm 8 W UV tubes with an overall intensity of 1150 μW/cm$^2$ at a distance of 7.6 cm. The polymerization reaction was allowed to proceed for 3 hours to afford a porous polymer monolith with a pore diameter of 13.2 μm. The temperature in the photoreactor was kept at 20° C. by a continuous flow of pressurized air.

After the polymerization was completed, a 25 μm i.d. and 50 cm long fused silica capillary was attached to the microchip inlet access hole using epoxy glue. The other end of this capillary was connected to a programmable micropump and the monolith within the microchannel was washed at a flow rate of 0.5 μL/min with methanol to remove all unreacted components from its pores.

Example 2

Solid Phase Extraction of Small Molecules in Ion Exchange Mode

A 600 μmol/L stock solution of Coumarin 519 (Sigma, St. Louis, Mo.) was prepared by dissolving 8.6 mg of this compound in 50 mL of acetone. The stock solution was then diluted with deionized water to give a final concentration of 10 nmol/L. A 200 μL injection loop was filled with this solution and this solution pumped through the ion-exchange concentrator of Example 1 at a flow rate of 3 μL/min.

Figure 2:
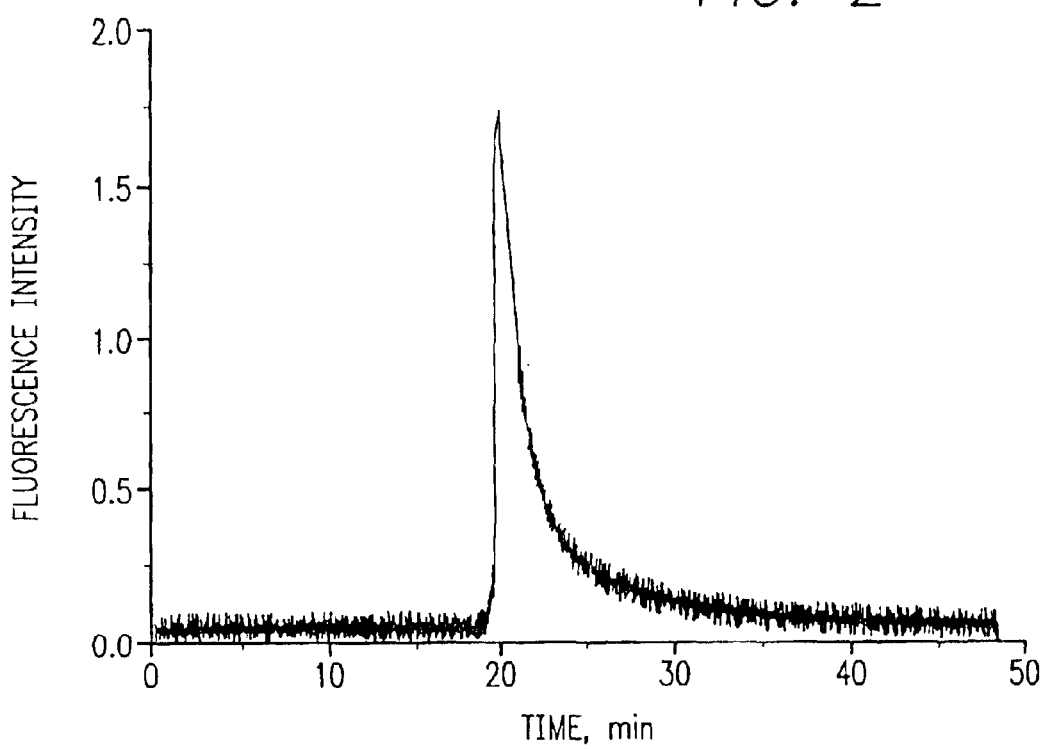
FIG. 2 shows elution profile of Coumarin 519 from ion-exchange concentrator. Conditions: Loading: 200 $\mu$L of 10 nmol/L Coumarin 519, flow rate 3 $\mu$L/min. Elution: 10 s pulses of 1.0 mol/L sodium salicylate, flow rate 203 nL/min.

The adsorbed Coumarin 519 was eluted using 10 s long pulses of 0.5 mol/L aqueous sodium salicylate at a flow rate of 203 nL/min to create a peak shown in FIG. 2.

These conditions afford almost complete elution and a concentration enhancement by a factor of 190. The concentrating function of the device was regenerated by washing the monolith within the microchannel with a 1:1 mixture of 0.1 mol/L HCl and acetonitrile.

Release of the Coumarin 519 probe from the concentrator was monitored by measuring the intensity of fluorescence and visualized as a peak. The concentration enhancement was then calculated by dividing the volume of probe solution used in the adsorption step by the volume of the eluted peak. The peak represents the eluted product of which width depends on the flow rate.

From the results seen in FIG. 2, the total adsorption capacity is estimated to be at least $2 \times 10^{-12}$ mol representing a volumetric capacity of $6.6 \times 10^{-5}$ mol/L.

Further increase in capacity may be achieved by using monoliths containing a higher percentage of META.

Example 3

Microfluidic Device For Solid Phase Extraction in Hydrophobic Interaction Mode

The microfluidic device for solid phase extraction in the hydrophobic interaction mode was prepared using procedure identical with that of Example 1 except that the polymerization mixture was prepared by mixing 0.46 g of ethylene dimethacrylate (Sartomer, Exton, Pa.), 0.72 g butyl methacrylate, 12 mg azobisisobutyronitrile, 2.52 g methanol, and 1.08 g hexane. After purging with nitrogen, in situ photopolymerization, and washing using methods described in Example 1, the resulting monolith has a pore diameter of 19.5 μm.

Example 4

Solid Phase Extraction of Small Molecules in Hydrophobic Interaction Mode

Coumarin 519 was dissolved in a mixture of 0.8 mol/L ammonium sulfate and 10 mmol/L HCl to form a 10 nmol/L solution. A 200 μL injection loop was filled with this solution and this solution pumped through the hydrophobic concentrator of Example 3 at a flow rate of 3 μL/min.

Figure 3:
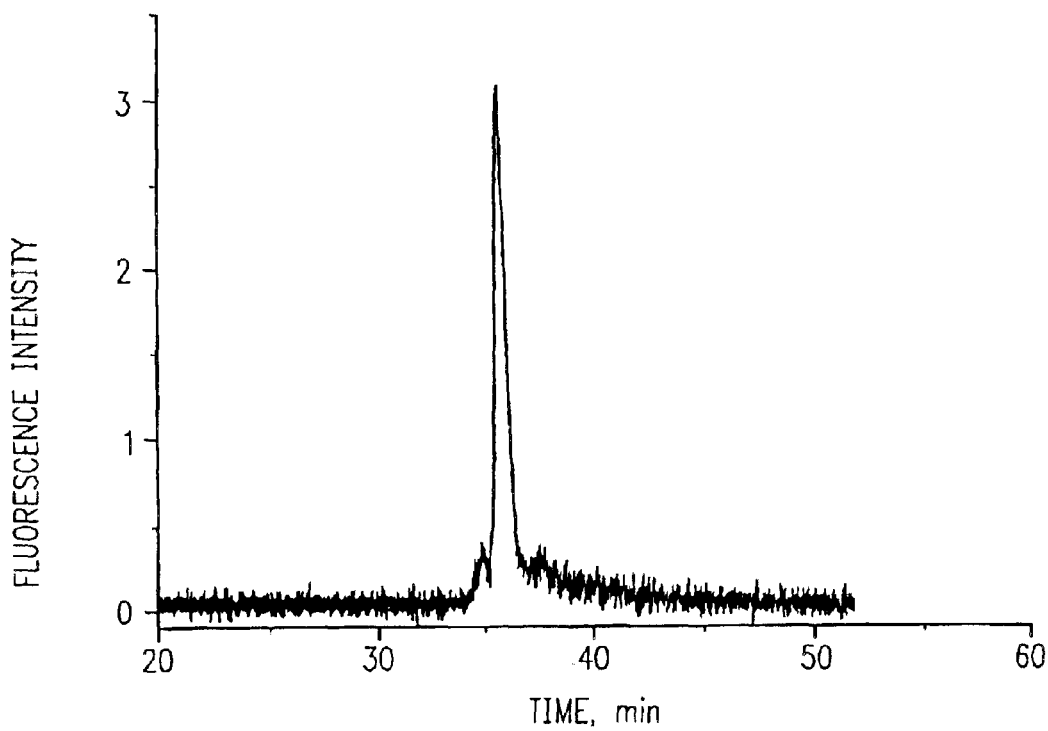
FIG. 3 shows elution pattern of Coumarin 519 from hydrophobic concentrator. Conditions: Loading: 200 $\mu$L of 10 nmol/L coumarin 519, flow rate 3 $\mu$L/min. Elution: acetonitrile, flow rate 115 nL/min.

The absorbed Coumarin 519 was released from the solid phase extractor using acetonitrile at a flow rate of 115 nL/min. Simple calculation using the elution peak shown in FIG. 3 reveals an 1650× increase in Coumarin 519 concentration. When the flow rate was raised to 761 or 3000 nL/min, respectively, the concentration enhancement was substantially decreased.

Table 5 illustrates an effect of flow rate on concentration enhancement of Coumarin 519 probe using the hydrophobic concentrator.

TABLE 5

Effect of Flow-Rate on Enrichment of Coumarin 519

| Flow rate nL/min | Concentration enhancement |
| --- | --- |
| 3000 | 337 |
| 761 | 905 |
| 115 | 1650 |

Table 5 shows enrichment of Coumarin 519 eluted from hydrophobic concentrator. Elution was performed with acetonitrile at flow rates of 3000, 761 and 115 nL/min. Results seen in Table 5 show that the flow rate has a significant effect on the extent of the concentration enhancement of the Coumarin probe.

As seen in Table 5, while a concentration enhancement of only 337 times was achieved at a flow rate of 3000 nL/min, a higher enhancement of 906 times was seen at flow rate 761 nL/min and even higher enhancement of 1650 times was obtained at a flow rate of 115 nL/min.

Example 5

Solid Phase Extraction of Peptides in Hydrophobic Interaction Mode

The Coumarin 519-peptide conjugate was prepared by reaction of 4.5 mg of Coumarin 519 acid chloride with 2.5 mg gly-phe-gly (Sigma, St. Louis, Mo.) in the presence of 10 µL triethylamine in 3 mL of DMF. This mixture was stirred at room temperature overnight, and the desired product recovered by column chromatography. The identity of the conjugate was verified by mass spectrometry. This conjugate was dissolved in deionized water to achieve a concentration of 10 nmol/L. Using the loop, 200 µL of this solution were pumped through the hydrophobic concentrator of Example 3 at a flow rate of 3 µL/min. Elution was achieved with a continuous flow of acetonitrile at a flow rate of 0.5 µL/min. According to the elution peak of FIG. 4, the concentration of the dye-peptide conjugate released using acetonitrile is increased 1320 times.

Figure 4:
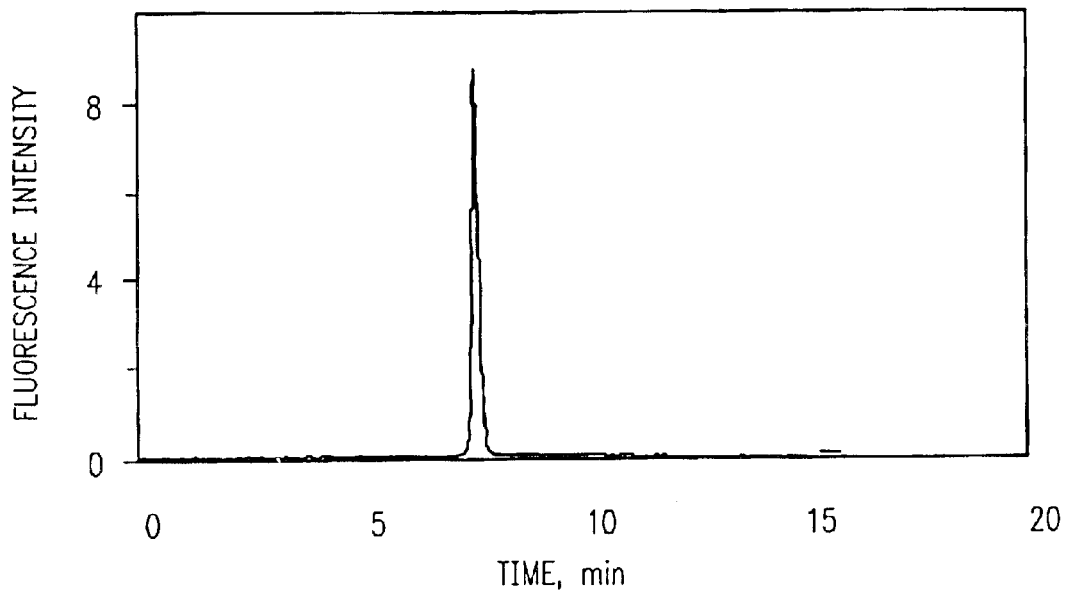
FIG. 4 shows elution of tetrapeptide labeled with Coumarin 519 from hydrophobic monolithic concentrator. Conditions: loading: 200 $\mu$L of 10 nmol/L peptide solution in water, flow rate 3 $\mu$L/min. Continuous elution with acetonitrile at a flow rate of 506 nL/min.

Results of these studies are seen in FIG. 4 which shows elution of tetrapeptide labeled with Coumarin 519 from hydrophobic monolithic concentrator. Conditions for loading of Coumarin 519 were: 200 µL of 10 nmol/L peptide solution in water, flow rate 3 µL/min. Elution was achieved with continuous flow of acetonitrile at a flow rate of 506 nL/min.

Using this approach, the concentration of the dye-peptide conjugate released using acetonitrile at a flow rate of 0.5 µL/min increased 1320 times (FIG. 4).

Example 6

Solid Phase Extraction of Peptides in Hydrophobic Interaction Mode

Using extraction conditions identical to those of Example 5, Coumarin 519-peptide conjugate was adsorbed on the monolith of Example 3. Elution was achieved with a 30 s long pulse of acetonitrile that enabled recovery of all probe molecules and led to a concentration enhancement of 520.

Example 7

Solid Phase Extraction of Protein in Hydrophobic Interaction Mode

Figure 5:
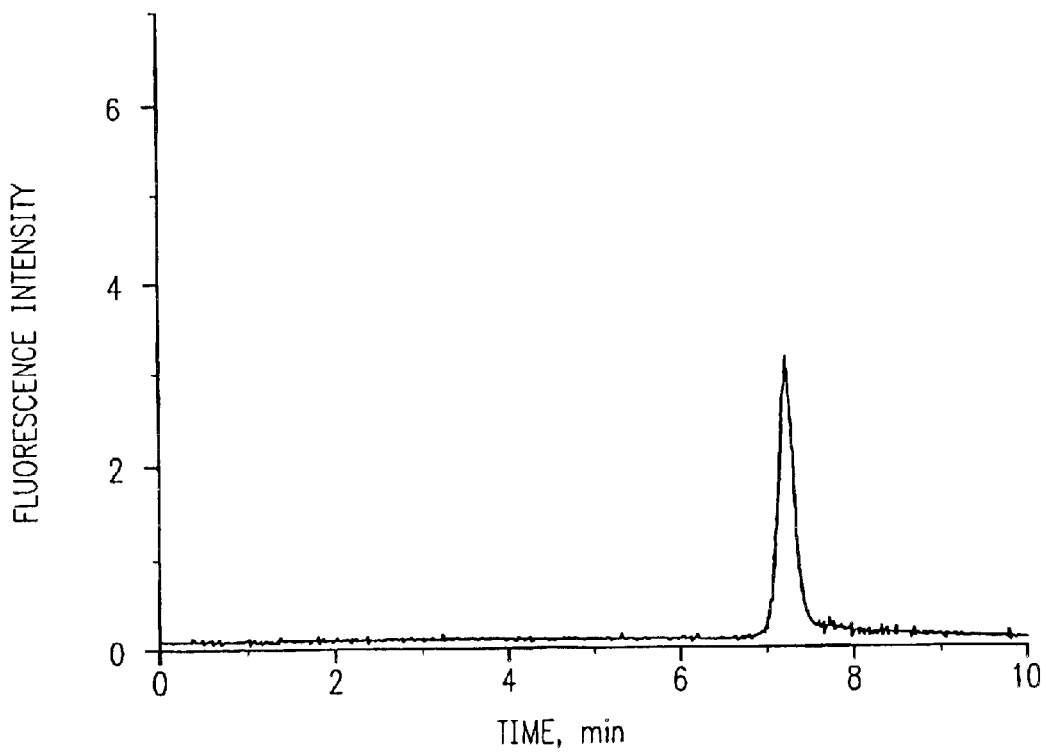

Recombinant green fluorescent protein (GFP) obtained from Clontech Laboratories, Inc. (Palo Alto, Calif.), consisting of 238 amino acid residues and having a molecular weight of 27,000 was dissolved in 0.95 mol/L ammonium sulfate/8 mmol/L Tris-HCl buffer pH 8.0 to make a 0.5 mg/mL (18.5 nmol/L) solution. The concentrating ability of the hydrophobic monolith of Example 3 for this protein was tested using 200 µL of the solution that was pumped at a flow rate of 3 µL/min through the monolith. The protein was released as shown in FIG. 5 using 1:1 water-acetonitrile mixture. A sample enrichment of 1002 was achieved at a flow rate of 0.53 µl/min. When illuminated with blue or UV light, GFP yields a bright green fluorescence. Since GFP is less hydrophobic, its adsorption was carried out from solution in 0.95 mol/L ammonium sulfate in 8 mmol/L TRIS-HCl buffer pH 8.0. Once again, 200 µL of 18.5 nmol/L G.F.P. solution was pumped through the monolith at a flow rate of 3 µL/min. The protein was released using 1:1 water-acetonitrile mixture. Results of these studies are seen in FIG. 5.

Results show that while a sample enrichment of 355 times was obtained at a flow rate of 3 µL/min, this value increased to 756 at 1.03 µL/min and to 1002 at 0.53 µL/min).

FIG. 5 shows elution pattern of GFP from hydrophobic monolithic concentrator. Conditions for loading of GFP were: 200 µL of 18.5 nmol/L protein solution in 8 mmol/L TRIS-HCl buffer (pH 8) containing 0.95 mol/L ammonium sulfate, flow rate 3 µL/min; Elution was achieved with 1:1 acetonitrile-water at a flow rate of 3 (1), 1.03 (2), and 0.53 µL/min (3).

Example 8

Microfluidic Device for Concentration in Affinity Mode

Benzophenone (1% with respect to monomers) was dissolved in a polymerization mixture consisting of 24% glycidyl methacrylate, 16% ethylene dimethacrylate, 42% t-butanol, and 18% cyclohexanol. This mixture was purged with nitrogen for 10 min to remove oxygen.

The methacryloylated microchip channel was completely filled with the deaerated polymerization mixture using a syringe and the openings sealed with tape. The surface of the chip was then covered with a mask that had an open window allowing a specific section of the channel to be exposed to the UV light. The microchip was then covered with foil except for the 7 mm long window, and exposed to UV light with a radiation power of 15 mWcm-2 in a photoreactor. The polymerization reaction was allowed to proceed for 3 hours to afford a porous polymer monolith with a pore diameter of 2.02 µm.

The affinity ligand was then attached to the pore surface in the monolith. A 30 mg/mL tannic acid solution in water which pH value was adjusted by dilute HCl to 3.5 was pumped through this monolith at a flow rate of 10 µL/min for 30 min. Once the reaction of tannic acid was completed, the residual epoxide groups were quenched by hydrolysis carried out by pumping 0.5 mol/L aqueous sulfuric acid through the monolith at a room temperature for 5 hours.

Example 9

Solid Phase Extraction of Protein in Affinity Mode

Figure 6:
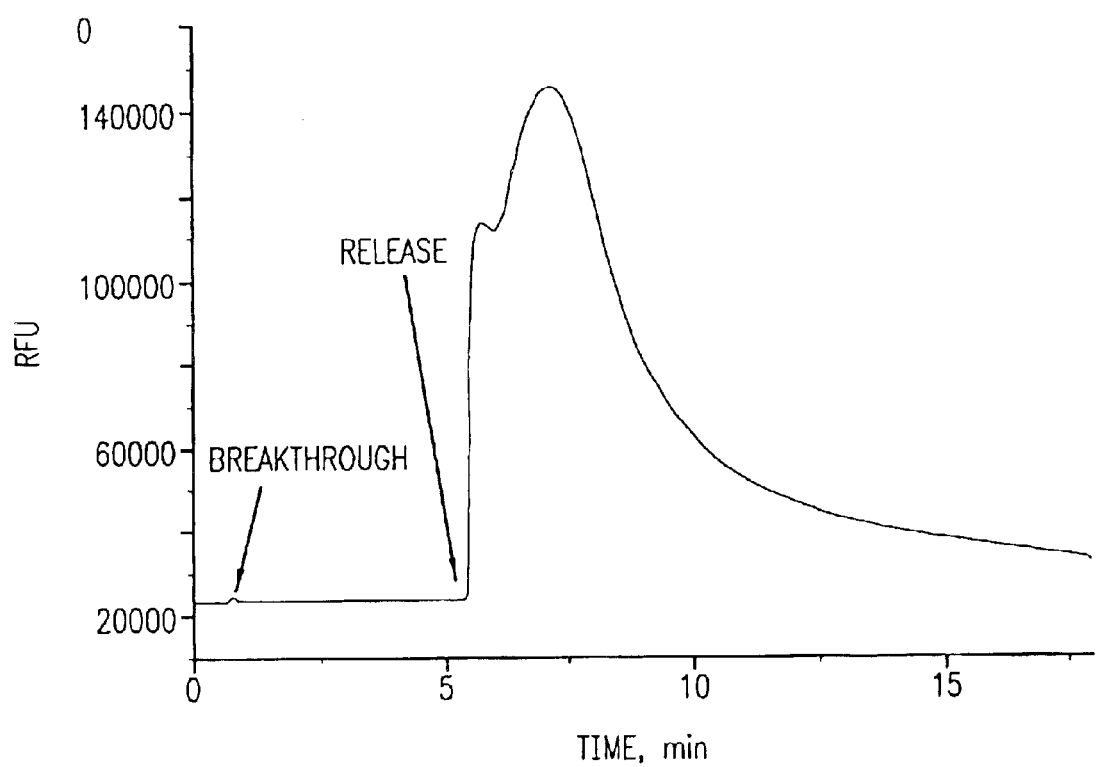
FIG. 6 shows elution profile of fluorescein isothiocyanate modified ovalbumin from a monolithic concentrator consisting of poly(glycidyl methacrylate-co-ethylene dimethacrylate)monolith with chemically attached tannic acid. Conditions under which sorption and elution was performed are as follows: Sorption: 20 $\mu$L of 0.2 $\mu$g/mL solution of fluorescein isothiocyanate labeled ovalbumin in phosphate buffer pH 7.0, flow rate of 10 $\mu$L/min. Elution: 20 $\mu$L of aqueous sodium hydroxide solution, pH 10.

Fluorescein isothiocyanate labeled ovalbumin was dissolved in phosphate buffer pH 7.0 to make a 0.2 mg/mL solution. The concentrating ability of the affinity monolith of Example 8 for this protein was tested using 20 µL of the solution that was pumped at a flow rate of 10 µL/min through the affinity monolith. The protein was released using 20 µL of an aqueous sodium hydroxide solution pH 10. An enrichment of 102 was achieved for the fluorescein isothiocyanate labeled ovalbumin as shown in FIG. 6.

Example 10

In situ Photopolymerization

The monomer mixtures shown in Table 2 were purged with nitrogen gas for 5 min. The top of the microdevice shown in FIG. 1B was covered with a mask (shown in FIG. 1D). The channels filled with the deaerated polymerization mixture using a syringe, and the microchip was exposed to UV-light from an Oriel deep UV illumination system series 8700 (Stratford, Conn.) fitted with a 500 W HgXe-lamp. The radiation power was measured using an OAI Model 354 exposure monitor (Milpitas, Calif.).

After the desired polymerization time elapsed, the device was aligned between two aluminum plates with the top one containing holes suitable for the attachment of chromatographic fittings, connected to a syringe pump (model 100 DM, ISCO, Lincoln, Nebr.), and the channels were washed with methanol for 12 hours at a flow rate of 1 µL/min. The flow resistance (back pressure) was then measured for flow rates in the range of 0.1–3 µL/min. Finally, the chip was removed from the holder and fused silica capillaries (Polymicro Technologies, Phoenix, Ariz.) were affixed to its holes using a two-component epoxy glue.

Example 11

Detection of Mixing of the Fluids in the Monolith Mixer

Mixing of the two fluids in the monolith mixer was observed in an inverted microscope (Nikon Eclipse TE200) equipped with a multiband dual FITC-Texas Red epi-fluorescence filter block and a 4× objective. Solutions of two fluorescence dyes, 5(6)-carboxyfluorescein (0.050 mmol/L) and Rhodamine B (0.125 mmol/L), both in 10 mmol/L borate buffer in 3:1 methanol-water, pH=9.2, were pumped simultaneously through the side channels at equal flow rates using a double syringe pump (Model 101, kd Scientific, New Hope, Pa.).

The mixing length was determined visually. Using the stage, the field observed through the microscope was moved down the channel to the point at which complete mixing characterized by a homogeneous orange-brown color all across the channel was observed. This procedure was repeated at least two times and the average value was used as the mixing length. This method is reproducible with an error of less than ±0.5 mm.

What is claimed is:

1. A microfluidic device for extracting, concentrating, or mixing, comprising a porous polymer monolith portions of a microchannel formed by a process comprising polymerizing selected areas of a mixture in said microchannel enabling a fluid flow, said porous polymer having pores of sizes in a range selected from the group of ranges consisting of: (a) about 10 µm to about 20 µm and (b) about 30 nm to about 1 µm, and further comprising at least one polymerized monomer unit bearing a hydrophilic group, a precursor of a hydrophilic group, an ionizable group, a precursor of an ionizable group, an affinity ligand, or a mixture thereof.

2. The device of claim 1, wherein the porous polymer monolith is a porous organic polymer further comprising ethylene dimethacrylate.

3. The device of claim 1, wherein the porous polymer monolith comprises polymerized monomer units bearing a hydrophilic group or a precursor to a hydrophilic group selected from the group consisting of 2-hydroxyethyl methacrylate, 2-hydroxyethyl acrylate, glycidyl methacrylate, glycidyl acrylate, acetoxystyrene, t-butoxycarbonyloxystyrene, and a combination thereof.

4. The device of claim 1, wherein the porous polymer monolith comprises polymerized monomer units bearing an ionizable group selected from the group consisting of acrylic acid, methacrylic acid, itaconic acid, maleic anhydride, styrene sulfonic acid, 2-acrylamido-2-methyl-3-propanesulfonic acid, 2-(methacryloxy)ethylphosphate, acrylic amide of amino acid, methacrylic amide of amino acid, 2-vinylpyridine, 4-vinylpyridine, 2-(dialkylamino) ethyl acrylate, methacrylate 2-(dialkylamino)ethyl, 2-(morpholino)ethyl acrylate, 2-(morpholino)ethyl methacrylate, [2-(methacryloxy)ethyl]trimethylammonium chloride, [2-methacryloxy)ethyl]trimethylammonium methylsulfonate, and a combination thereof.

5. The device of claim 1, wherein the porous polymer monolith comprises polymerized monomer units bearing a biological affinity ligand selected from the group consisting of polysaccharides, antibodies, enzymes, lectins, antigens, cell surface receptors, intracellular receptors, viral coat proteins, DNA, and a mixture thereof, or a synthetic affinity ligand selected from the group consisting of reactive dyes, tannic acid, gallic acid, iminodiacetic acid, ethylenediaminetriacetic acid, inert salt of [2-(methacryloyloxy) ethyl] dimethyl(3-sulfopropyl)ammonium hydroxide, and a mixture thereof.

6. The device of claim 1, wherein porous polymer monolith comprises from about 10 to about 90% of one or more monovinyl monomers and about 5 to about 90% of one or more polyvinyl monomers.

7. The device of claim 1, wherein said microchannel enabling fluid flow is created within a solid support material.

8. The device of claim 7, wherein said solid support material is glass, silica, quartz, or plastic.

9. A method for formation of mixtures of two or more fluids using device of claim 1.

10. A method for concentration or extraction of compounds from their solutions using device of claim 1.

11. The device of claim 1 wherein said porous polymer has at least 50% porosity.

12. A method for fabricating a microfluidic device suitable for extraction, concentration, or mixing, said method comprising steps:

(a) providing an inert solid substrate;

(b) generating a single or multiple microchannels contoured into said solid substrate;

(c) forming a polymerization mixture by admixing a monovinyl monomer, a cross-linking monomer, an initiator, and a porogenic solvent;

(d) introducing the polymerization mixture, with sufficient porogen to form pores in a range of either (i) about 30 nm to about 1 µm or (ii) about 10 µm to about 20 µm, into a microchannel within a microfluidic device; and (e) initiating the in situ polymerization of the mixture by means of exposing to initiator only selected portions of the mixture, thereby forming a monolithic polymer within portions of the microfluidic channel.

13. The method of claim 12, wherein the monomer comprises a hydrophilic group, a precursor of a hydrophilic group, an ionizable group, or a hydrophobic group selected from the group consisting of acrylate esters, methacrylate esters, acrylate amides, methacrylate amides, styrene, styrene derivatives, and a combination thereof.

14. The method of claim 13, wherein the monomer comprises a hydrophilic group or a precursor to a hydrophilic group selected from the group consisting of 2-hydroxyethyl methacrylate, 2-hydroxyethyl acrylate, glycidyl methacrylate, glycidyl acrylate, acetoxystyrene, t-butoxycarbonyloxystyrene, and a combination thereof.

15. The method of claim 13, wherein the monomer comprises a hydrophobic group selected from the group consisting of alkyl acrylate, alkyl methacrylate, styrene, alkylstyrenes, and a combination thereof.

16. The method of claim 13, wherein the ionizable monomer comprises an amino group, a carboxylic acid group, a sulfonic or phosphonic acid group.

17. The method of claim 16, wherein the ionizable monomer is selected from the group consisting of acrylic acid, methacrylic acid, itaconic acid, maleic anhydride, styrene sulfonic acid, 2-acrylamido-2-methyl-3-propanesulfonic acid, 2-(methacryloxy)ethylphosphate, acrylic amide of amino acid, methacrylic amide of amino acid, 2-vinylpyridine, 4-vinylpyridine, 2-(dialkylamino)ethyl acrylate, methacrylate, [2-(dialkylamino)ethyl]2-(morpholino)ethyl acrylate, 2-morpholino)ethyl methacrylate, [2-(methacryloxy)ethyl]trimethylammonium chloride, [2-methacryloxy)ethyl]trimethylammonium methylsulfate, and a combination thereof.

18. The method of claim 13 additionally comprising an affinity ligand.

19. The method of claim 18, wherein the affinity ligand is a biologic or synthetic compound.

20. The method of claim 19, wherein the biological affinity ligand is selected from the group consisting of polysaccharides, antibodies, enzymes, lectins, antigens, cell surface receptors, intracellular receptors, viral coat proteins, DNA, and a mixture thereof.

21. The method of claim 19, wherein the synthetic affinity ligand is selected from the group consisting of reactive dyes, tannic acid, gallic acid, iminodiacetic acid, ethylenediaminetriacetic acid, inert salt of [2-(methacryloyloxy) ethyl] dimethyl(3-sulfopropyl)ammonium hydroxide, and a mixture thereof.

22. The method of claim 12, wherein the cross-linking monomer is a polyvinyl monomer.

23. The method of claim 22, wherein the polyvinyl monomer is a diacrylate, dimethacrylate, triacrylate, trimethacrylate, diacrylamide, dimethacrylate, or a divinylaromatic monomer.

24. The method of claim 23, wherein the polyvinyl monomer is ethylene diacrylate, ethylene dimethacrylate, trimethylolpropane triacrylate, trimethylolpropane trimethacrylate, methylenebisacrylamide, or piperidinediacrylamide.

25. The method of claim 23 wherein the polyvinyl monomer is divinylbenzene or divinylnaphthalene.

26. The method of claim 12, wherein said initiator is photoinitiator, redox, or thermal initiator.

27. The method of claim 26, wherein said photoinitiator is selected from the group consisting of benzophenone, dimethoxyacetophenone, xanthone, and thioxanthone.

28. The method of claim 26, wherein said thermal initiator is a peroxide, a hydroperoxide, or an azo compound.

29. The method of claim 28, wherein said thermal initiator is selected from the group consisting of benzoylperoxide, potassium peroxodisulfate, ammonium peroxodisulfate, t-butyl hydroperoxide, azobisobutyronitrile, and azobisisocyanobutyric acid.

30. The method of claim 26, wherein said redox initiator is selected from the group consisting of mixtures of benzoyl peroxide-dimethylaniline, and ammonium peroxodisulfate-N,N,N'N'-tetramethylene-1,2-ethylenedimanine.

31. The method of claim 12, wherein said porogenic solvent is water or an organic solvent or a mixture thereof.

32. The method of claim 31, wherein said porogenic solvent is water.

33. The method of claim 31, wherein said porogenic solvent is an organic solvent selected from the group consisting of hydrocarbons, alcohols, ketons, aldehydes, organic acid esters, soluble polymer solutions, and mixtures thereof.

34. The method of claim 33, wherein said porogenic solvent is selected from the group consisting of cyclohexanol, 1-dodecanol, methanol, hexane, propanol, dodecanol, ethylene glycol, butanediol, methyl-t-butylether, diisopropylketone, butanal ethyl acetate, butyl acetate, poly (methyl methacrylate), and mixture thereof.

35. The method of claim 31 wherein the solvent is present in an amount about 30 vol % to about 80 vol %.

36. The method of claim 35 wherein the solvent is present in an amount from about 40 vol % to about 60 vol %.

37. The method of claim 12, wherein the initiating step is achieved by irradiation, admixing of redox components, or heating.

38. The method of claim 37, wherein the irradiation is irradiation with ultraviolet light.

39. The method of claim 37 wherein the redox components are ammonium peroxodisulfate and N,N,N',N'-tetramethylene-1,2-ethylenedimanine.

40. The method of claim 37, wherein the heating is performed at a temperature from about 30° C. to about 120° C.

41. A method for concentrating a composition in a microfluidic device, comprising:
(a) providing and inert solid substrate having a microchannel wherein portions of the microchannel has a fluid path passing through pores defined by microglobules in a crosslinked polymer monolith formed from an acrylate, methacrylate or styrene monomer and formed by a process comprising polymerizing selected areas of a mixture in said microchannel crosslinked with a polyvinyl monomer;
(b) passing a first fluid containing the composition to be concentrated through the polymer monolith so that the composition is absorbed onto the microglobules; and
(c) passing a second fluid through the polymer monolith whereby the composition is eluted as a single fraction.

42. The method of claim 41 wherein the second fluid for elution comprises a material selected from the group consisting of: sodium salicylate, acetonitrile and other sodium salt solution.

* * * * *

UNITED STATES PATENT AND TRADEMARK OFFICE
CERTIFICATE OF CORRECTION

PATENT NO. : 6,887,384 B1
DATED : May 3, 2005
INVENTOR(S) : Jean M. J. Frechet et al.

It is certified that error appears in the above-identified patent and that said Letters Patent is hereby corrected as shown below:

Column 19,
Line 55, insert -- within -- after "monolith".

Column 20,
Line 62, delete "selected".

Column 21,
Line 32, delete "biologic" and insert therefor -- biological --.
Line 48, delete "dimethacrylate" and insert therefor -- dimethacrylamide --.

Column 22,
Line 6, delete "azobisobutyronitrile" and insert therefor -- azobisisobutyronitrile --.
Line 17, delete "ketons" and insert therefor -- ketones --.
Line 18, insert -- ethers, -- after "esters,".
Line 43, delete "and" and insert therefor -- an --.
Line 59, delete "solution" and insert therefor -- solutions --.

Signed and Sealed this

Eleventh Day of October , 2005

JON W. DUDAS
*Director of the United States Patent and Trademark Office*